United States Patent
Eraker et al.

(10) Patent No.: US 6,662,051 B1
(45) Date of Patent: Dec. 9, 2003

(54) PROGRAMMABLE PAIN REDUCTION DEVICE

(76) Inventors: Stephen A. Eraker, 11908 Southern Lites Dr., Clackamas, OR (US) 97015; Sarah J. Eraker, 119085 Southern Lites Dr., Clackamas, OR (US) 97015; David B. Eraker, 66 Bell #100, Seattle, WA (US) 98121-3610

(*) Notice: Subject to any disclaimer, the term of this patent is extended or adjusted under 35 U.S.C. 154(b) by 218 days.

(21) Appl. No.: 09/824,766

(22) Filed: Apr. 2, 2001

Related U.S. Application Data (60) Provisional application No. 60/193,675, filed on Mar. 31, 2000.

(51) Int. Cl.[7] ............................................. A61N 1/362
(52) U.S. Cl. ...................................................... 607/59
(58) Field of Search ....................... 128/920; 600/300; 607/5, 30, 59, 46; 125/923–925, 920

(56) References Cited

U.S. PATENT DOCUMENTS

| | | | |
|---|---|---|---|
| 2,622,601 A | 2/1952 | Nemee | 128/422 |
| 2,771,554 A | 11/1956 | Gratzl | 250/27 |
| 2,808,826 A | 10/1957 | Reiner | 128/2.1 |
| 4,019,519 A | 4/1977 | Geerling | 128/423 |
| 4,084,595 A | 4/1978 | Miller | 128/422 |
| 4,340,063 A | 7/1982 | Maurer | 128/421 |
| 4,431,002 A | 2/1984 | Maurer | 128/422 |
| 4,442,839 A | 4/1984 | Maurer | 128/419 |
| 4,531,527 A | 7/1985 | Rinhold et al. | 128/696 |
| 4,556,064 A | 12/1985 | Pomeranz | 128/423 |
| 4,712,562 A | 12/1987 | Ohayou | 128/670 |
| 4,759,368 A | 7/1988 | Spanton | 128/421 |
| 4,838,275 A | 6/1989 | Lee | 128/633 |
| 4,926,865 A | 5/1990 | Oman | 128/421 |
| 4,949,721 A * | 8/1990 | Toriu et al. | 607/46 |
| 5,003,984 A | 4/1991 | Muraki | 128/904 |
| 5,012,411 A | 4/1991 | Policastro | 364/413.06 |
| 5,184,617 A | 2/1993 | Harris | 128/419 |
| 5,458,625 A | 10/1995 | Kendall | 607/45 |
| 5,607,460 A | 3/1997 | Kroll | 607/30 |
| 5,653,739 A | 8/1997 | Maurer | 607/46 |
| 5,810,747 A | 9/1998 | Brudny | 600/595 |
| 5,822,715 A | 10/1998 | Worthington | 600/309 |
| 5,836,993 A | 11/1998 | Cole | 607/2 |
| 5,861,017 A * | 1/1999 | Smith et al. | 607/49 |
| 5,873,900 A | 2/1999 | Maurer | 607/46 |

(List continued on next page.)

OTHER PUBLICATIONS

Melzack, R, et al. "Pain Mechanisms: A New Theory." Science, vol. 150, (Nov. 19, 1965) pp 971–979.

Hughes, J, et al. "Identification of Two Related Pentapeptides From the Brain with Potent Opiate agonist Activity." Nature, vol. 258, (Dec. 18, 1975) pp. 577–579.

Han, J. "The neurochemical Basis of Pain Relief by Acupuncture, vol. 2". Beijing China. Hubei Science and Technology Press 1998, Chapters 1 and 9.

Ulett, G. "Beyond Yin and Yang: How Acupuncture Really Works," St. Louis. Warren H. Green, Inc., 1992, Chapter III.

Primary Examiner—George R. Evanisko
(74) Attorney, Agent, or Firm—Marger Johnson & McClollom, PC (57) ABSTRACT

A remotely programmable medical device having a memory for storing a program, a patient interface (electrodes, syringe, etc.), and a microprocessor for operating the patient interface under the control of the program. The program is constructed by a remote knowledge based analysis tool (database with fuzzy logic), accessible by the medical device over a network such as the Internet. The program, responsive to patient data entered into a client computer on the network, is then transmitted to the medical device as through the client computer to which the medical device is coupled via an interface docking terminal. The remotely programmed medical device is then used on the patient. Transcutaneous electrical nerve stimulation (TENS) devices are preferably programmed to output electrical stimulus signals of alternating high (80–100 Hz) and low frequency (2–5 Hz) with symmetric increase and decrease in waveform amplitude.

17 Claims, 5 Drawing Sheets

U.S. PATENT DOCUMENTS

| | | | |
|---|---|---|---|
| 5,935,060 A | 8/1999 | Iliff | 600/308 |
| 5,935,156 A | 8/1999 | Chandler | 607/66 |
| 5,960,403 A | 9/1999 | Brown | 705/2 |
| 6,012,034 A | 1/2000 | Hamparian | 705/2 |
| 6,022,315 A | 2/2000 | Iliff | 600/308 |
| 6,024,539 A | 2/2000 | Blomquist | 417/63 |
| 6,148,814 A | 11/2000 | Clemmer | 128/208.24 |
| 6,168,563 B1 | 1/2001 | Brown | 600/301 |
| 6,308,102 B1 * | 10/2001 | Sieracki et al. | 607/59 |
| 6,427,083 B1 * | 7/2002 | Owen et al. | 607/5 |
| 6,459,933 B1 * | 10/2002 | Lurie et al. | 607/5 |
| 2001/0056227 A1 * | 12/2001 | Gopinathan et al. | 600/300 |

* cited by examiner

PAIN REDUCTION DEVICE
FIG. 4

PROGRAMMABLE PAIN REDUCTION DEVICE

CROSS-REFERENCES TO RELATED APPLICATIONS

This application claims the benefit from U.S. Provisional Patent Application No. 60/193,675 filed Mar. 31, 2000 whose contents are incorporated herein for all purposes.

BACKGROUND OF THE INVENTION

1. Field of the Invention

This invention relates generally to a pain treatment device, and more particularly to transcutaneous electrical nerve stimulation (TENS) devices and methods for programming and operating such devices to maximize effectiveness.

2. Description of the Prior Art

Chronic pain plagues over 100 million Americans on a daily basis. Many health regimens have been developed to alleviate chronic pain involving a variety of evidence-based and nonevidence-based therapies. Pain treatment programs usually involve pharmacological agents or neurosurgical/anesthesia based interventions. Unfortunately, some of the most effective treatments have serious side effects, lose their potency with prolonged use, result in dependence or are prescribed in inadequate amounts. Because of this, the search for pain treatment programs has involved a variety of adjuvant treatments including transcutaneous electrical nerve stimulation (TENS) and acupoint stimulation (acupuncture).

TRANSCUTANEOUS ELECTRICAL NERVE STIMULATION(TENS)

Although there were efforts to utilize electrical stimulation to suppress pain 2000 years ago, a detailed, scientific investigation was finally conducted by Professor Galvani of the University of Bologna in the early 1800s. In 1967, Dr. Sweet developed one of the first modem electrical apparatus for suppression of organic pain. TENS (transcutaneous electrical nerve stimulation) is a procedure that applies controlled bursts of electrical impulse on the skin to the nervous system in order to reduce pain. A mild tingling sensation and possibly muscle twitch is felt by the patient using a TENS device. A TENS device can be used by a patient at varying locations numerous times throughout the day. TENS therapy is based on a non-invasive, non-narcotic concept of pain management. It is non-addictive, not subject to abuse and does not interact with drugs. TENS has been proven to be an effective modality in the treatment of a variety of organic pain problems including: chronic neck and back pain, bursitis, arthritic disease.

Although there are many theories as to transmission of pain from the nervous system to the brain, gate control and endorphin theory have emerged as the best and most generally accepted evidence based explanations for the efficacy of TENS in the treatment of pain. Melzack and Wall in 1965 described the Gate Control Theory of Pain (GCT). (Melzack, 1965) GCT states that pain can be inhibited and controlled by "closing the gate" on pain signals as they arrive at the central nervous system. Pain impulses traveling along a nerve, through the spinal cord, and to the brain can be modified at any point along the transmission route. Pain signals carried by small, slow conducting peripheral nerve fibers (C-fibers) can be blocked by many things including stimulation of the large diameter, rapidly conducting peripheral nerve fibers (A fibers). GCT occurs in a segment of the spinal cord containing many T-cells called the Substantia Gelatinosa. The balance between A and C fibers determines the degree of pain. Stimulation of A fibers by a variety of stimuli (scratching, pressure, vibration or high amplitude electrical stimulation) without much stimulation of C fibers, will close the gate. Unfortunately, the problem of accommodation requires more and more variation of treatment parameters to keep the gate closed to pain.

The major problem with electrical stimulation, however, continues to be accommodation, whereby the stimulated nerve accommodates itself over time to the electrical charge, diminishing the effectiveness of treatment. A variety of U.S. Pat. Nos. (e.g. 2,622,601, 2,771,554) involve TENS devices with the means to vary the rate, amplitude or pulse width of the generated electrical pulse. Unfortunately, accommodation would still occur unless an individual manually adjusted the controls prior to or during the treatment. The process was mentally and physically demanding and maximum pain relief was not provided. For example, U.S. Pat. No. 4,019,519 (Geerling) discloses a unit having only its amplitude adjustable. U.S. Pat. No. 4,084,595 (Miller), and U.S. Pat. No. 4,759,368 (Spanton) disclose TENS devices in which the stimulus signal has a manually and independently varied rate, amplitude and pulse width. To provide improved output pulse compensation, one TENS device (U.S. Pat. No. 5,184,617 to Harris et al.) provides manual adjustment of pulse width control linked to a predetermined change in range of intensity of the pulses. Although variation enabled one to deal with accommodation, pain relief was sacrificed due to the interaction between amplitude and pulse width. As the duration of pulse is shortened, amplitude must be increased to maintain the efficacy of stimulus. The relationship when plotted graphically is known as a strength-duration curve. Thus, not only must a TENS unit have adjustable amplitude and pulse width, but it must also be able to modulate those values to optimize pain relief.

In addition to amplitude and pulse width, the rate of pulses must vary so as to minimize accommodation. U.S. Pat. No. 2,808,826 (Reiner), disclosed a unit that permitted instantaneous changes in pulse width and amplitude to two pre-set points along the strength duration curve. U.S. Pat. Nos. 4,340,063, 4,431,002 and 4,442,839 (Maurer), disclose units with modulation of amplitude, pulse width, and repetition rates, but the problem of accommodation still existed.

Acupuncture

Acupuncture has existed in China for over 4,000 years, and it spread to Korea in 300 AD, to Japan in the 1600s and to Europe by the 1800s. Although mentioned in a surgical treatise by Billroth in 1863, and in Osler's 1912 *Principles and Practices of Medicine,* interest in the U.S. dramatically increased following Nixon's 1971 trip to China. The World Health Organization has indicated that over one third of the world's population is using acupuncture at the present time.

The discovery in 1975 that the pain receptors in the brain are blocked by a variety of endogenous opiate-like substances, including endorphins, was a major advance in the understanding of acupuncture. (Hughes 1975) Endorphin theory postulates that stimulation of the nervous system, by needles or more effectively by low frequency electrical current, will trigger the release of naturally occurring pain making morphine-like substances including endorphins and enkephalins. These naturally occurring substances block pain signals from reaching the brain by a mechanism similar to conventional drug therapy but without the side effects of morphine. Additional factors in the transmission and central amplification of pain signals involve the so-called NMDA receptor and the chemical neurotransmitter substance P. These substances can trigger long-term anatomical changes in both sensory and spinal nerves, making these cells more responsive to later pain stimulation. Endorphin theory and gate control theory have provided a generally accepted neurochemical explanation for the efficacy of acupuncture. (Han 1998)

The importance of proper acupuncture point location has been emphasized for over 3000 years. The traditional 360 physiologically active points were discovered by trial and error. Meridian theory and a variety of pre-scientific era explanations contributed to an increase to over 1000 points. Most of the useful points coincide with motor points and lie close to nerve trunks or Golgi tendon organs. Traditional and electrical acupuncture today may be practiced with knowledge of 50 physiologically active points. (Ulett, 1992)

The use of electrical stimulation of acupoints can be traced back to 1764 in Japan. It is generally accepted that general acupuncture with electrical stimulation increases the effectiveness of pain relief. Evidence based research about acupuncture and acupoint transcutaneous electrical nerve stimulation, however, continues to emphasize the critical importance of finding the proper location and parameters of stimulation for each individual. A circuit for electrotherapy and electronic acupuncture alternated a negative pulse train with a repetition rate of 100 and 500 Hz in groups with a repetition rate of 1 and 50 Hz with a positive bias provided for an integral of pulse train signals of zero is described in U.S. Pat. No. 4,556,064 (Pomeranz et al.). The signal was randomly switched sequentially from one skin stimulus site to another with application times that could be adjusted. Specific microcurrent waveform signals have also been patented in U.S. Pat. No. 5,935,156 (Chandler et al.). A specific acupoint stimulation device for a branch of the vagal nerve located in the ear is disclosed for substance withdrawal, pain relief, stress relief and or general muscle relaxation in U.S. Pat. No. 5,458,625 (Kendall).

Parameters for electrical stimulation are fortunately easier to apply and have been generally more effective than manual needling and manipulation. Locating and optimizing these 50 acupoints, however, continues to be difficult for health providers and is further complicated by the efficacy of multiple site stimulation.

Medical Data Analysis Technologies

There have been a number of previous patents relating to the measurement, transmission and analysis of health data with provision of therapeutic recommendations. A previous attempt at monitoring a patient's blood pressure and heart rate, sending the data via telephone to a remote central computer for storage and analysis with reports submitted to the physician or patient is described in U.S. Pat. No. 4,712,562 (Ohayon et al.). A similar system, with the receiving office unit automatically communicating with the physician under predetermined emergency circumstances is described in U.S. Pat. No. 4,531,527 (Reinhold et al.). A device for a patient to use electronics to measure multiple parameters is described in U.S. Pat. No. 4,838,275 (Lee). These data are electronically transmitted to a central surveillance and control office where a highly trained observer interacts with the patient. The observer conducts routine diagnostic sessions, except when an emergency is noted. Similarly, a portable self-contained apparatus for measuring, storing and transmitting detected physiological information to a remote location over a communication system is described in U.S. Pat. No. 5,012,411 (Policastro et al.). An apparatus for alerting a doctor, which provides an alarm corresponding to a patient and receives living body information signals transmitted through a transmitter, is described in U.S. Pat. No. 5,003,984 (Muraki et al.).

One electrotherapy device, such as a pacemaker, cardioverter or defibrillator, contains software code or instructions for operation stored in an attached memory device is described in U.S. Pat. No. 5,836,993 (Cole), but does not involve Internet or CNA. The programming and transmission of treatment parameters to a receiver of an implanted arrhythmia treatment device is described in U.S. Pat. No. 5,607,460 (Kroll et al.). An electronic pain rating scale which can alternatively include a dock and intensity sensor for recording a treatment session duration and intensity is described in U.S. Pat. Nos. 5,653,739 and 5,873,900 (Maurer et al.).

An interactive intervention transmission system used for monitoring a patient suffering from neurological movement disorders or seeking to improve skills performance and to assist in training is described in U.S. Pat. No. 5,810,747 (Brudny et al.). The patient station and supervision station can communicate with each other over the Internet or LAN. An expert system, fuzzy logic or a neural network is used to determine the goal to be achieved during the training. No modification of parameters involving a pain reduction or medical device is involved. A remotely programmable patient operated hand-held apparatus uses a communication network such as the world wide web to allow the health care provider to obtain patient data and to develop a script program is described in U.S. Pat. Nos. 5,822,715 (Worthington et al.) and 5,960,403 (Brown). The hand-help apparatus also obtains patient information supplied by a physiologic monitoring device, such as a blood glucose monitor in U.S. Pat. No. 6,168,563 (Brown).

A system and method for providing computerized, knowledge-based medical diagnostic and treatment advice using a network such as the Internet is found in U.S. Pat. Nos. 5,935,060 and 6,022,315 (Lliff). A system and method for communicating with an ambulatory delivery device, preferably a drug pump, both locally and remotely is described in U.S. Pat. No. 6,024,539 (Blomquist). A computer system comprising a control program for an intravenous device for infusion therapy based on input entered by the user is described in U.S. Pat. No. 6,012,034 (Hamparian et al.). The input and output interface will be in electrical communication with the computer device, but will not directly modify the parameter settings. A method and system for managing mechanical ventilator of patients uses data, processed according to a set of protocols and medical decision-making rules, to generate detailed executable instructions for patient care in U.S. Pat. No. 6,148,814 (Clemmer et al.). Patient care instructions can be carried out automatically or manually.

These patented devices, however, do not address situations where a portable piece of medical equipment is remotely programmed responsive to patient input criteria, and also do not involve the combination of Internet, CNA, and a patient or remote computer input/output interface. This is especially desired in the pain management field where self-administering patients often do not have the necessary background to properly program their portable TENS devices to address specific symptoms. Accordingly, a need remains for a system and method for addressing these deficiencies.

SUMMARY OF THE INVENTION

The present invention provides a method involving the use of Internet or combinations of network architectures to manage and treat chronic pain involving coordination between a patient, health providers, central computer with knowledge based program, remote computer with input/output interface and pain reducing device with input/output interface. The method includes a central computer with knowledge-based program to receive, store and analyze patient specific information. The patient or health provider will enter information into a remote computer terminal including: medical diagnoses, pain characteristics (including severity, characteristics, duration), patient functional status and patient psychosocial profile. Previous experience with evidence and non-evidence based treatment modalities will also be entered including: pharmacological pain treatment (pills or other drug-type forms), medical pain treatment, whether the treatment was non invasive or invasive (e.g. nerve blocks), physical and massage therapy, experience with pain reduction devices (e.g. transcutaneous electrical nerve stimulation (TENS)), chiropractic manipulation, traditional Chinese Medicine and homeopathy. The central computer with knowledge-based program can also be expanded to include other evidence based and non-evidence based treatment modalities.

The method includes a computer knowledge based program to receive, store and analyze patient specific information. The program helps a remote and/or central health provider to evaluate the effectiveness of pain treatment and makes specific patient recommendations regarding pain management and utilization and settings for a pain reduction medical device.

The information will be locally stored and transmitted from the entry terminal via Internet or combinations of network architectures to the knowledge base where data will be received stored and analyzed. An optional security layer will also be provided to prevent unauthorized access to the central computer. The security layer will comprise any standard security scheme or technology and may be used system wide as well as with all workstations, Internet applications, patients, and health providers. The central and/or remote medical provider, who can select to communicate to the remote health provider, patient or pain reduction device, will then review all knowledge based program recommendations. Patient data and pain reducing device data will be available for analysis on the three levels: manual, semiautomatic and automatic.

In the manual mode of operation, the knowledge-based program will primarily summarize data and perform minimal analysis. After reviewing the relevant pain data, the central health provider issues instructions to the patient and/or remote health provider via either textual commands on the PC monitor, voice and or video images or combinations of these facilities. Recommendations will be made regarding the particular location of optimal acupoint placement, as well as other treatment parameters including for example exercise, massage, or pharmaceutical therapy.

In semiautomatic mode, automated modification and analysis of patient responses will be added to the resources provided by the manual mode. The software knowledge based program will imitate the subjective methods for data analysis using heuristic means by using fuzzy logic.

Fuzzy logic is a branch of technology that solves problems, which include lexical uncertainty. Humans use words as subjective categories to classify parameters such as neck or back pain. While a concept may not be precisely defined, humans use them for complex evaluations and decisions that are used on many different factors. They do so by combining the rules that describe similar situations taking advantage of the flexibility in the definition of the words that constitute the rules. To implement these processes in engineering solutions, by a computer, requires a mathematical model. Fuzzy logic provides such a mathematical model and allows representation of human decisions and evaluation processes in algorithmic form. Although there are limits to what fuzzy logic can do, it can derive solutions for a given set of rules that have been defined for similar cases. If you can describe the desired performance of a technical system for certain distinct cases by rules, fuzzy logic will apply this knowledge to produce a solution. The optimal location of desired acupoints and nerve stimulation parameters is an excellent example of a problem that lends itself to resolution by fuzzy logic.

In the automatic mode, in addition to review of patient and pain reducing device data from the semi-automatic mode, treatment parameters will be recommend by using software based on an expert system. The expert system fixes the type of response to be attempted as well as the goals or parametric values to be achieved. The expert system used in this invention is a computer program that implements adductive reasoning or logic. This seeks to imitate the ways in which human beings draw logical conclusion in practice, even though the conclusions may be flawed. Thus, if one knows that a given predicate p implies that the predicate q and that q is true at the time it is sampled, we conclude that p must also be true. The result that p is now true can lead to additional adductive results and ultimately to some terminal results, which in this case is a recommendation regarding acupoint location and pain management. In the automatic mode, all treatment parameters are recommended by the software module. The medical professional will supervise and be able to intervene when the system is in semiautomatic or automatic modes.

Specific treatment recommendations will be provided including: location of optimal acupoints to treat a given chronic pain, treatment session parameters including number of treatments per day, and recommended duration. When the pain-reducing device is a transcutaneous electrical nerve stimulation (TENS) device, settings will be modified including: frequency, duration, polarity, and waveform. The preferred waveform parameters include: constant current output despite skin conductance changes, identical positive and negative square waves alternating with each other and having a net output of 0, automatic adjustment of pulse width with increase during low frequency stimulation and increase during high frequency stimulation, automatic adjustment of polarity, fixed and variable time intervals of 3 to 5 seconds of 2 to 4 Hz alternating with fixed and variable time intervals of 3 to 5 seconds of 80 to 100 Hz (with and without symmetrical increase and decrease in wave form).

In the preferred embodiment some of the information is transmitted directly to the pain-reducing medical device via the remote computer with. input/output interface regarding pain reduction medical device treatment parameters such as waveform, frequency, duration or polarity. It will also be possible to transmit this information to the patient or health professional in order to adjust the settings of the pain reduction device. Information may also be collected and stored in the pain reduction device and directly transmitted from the remote computer with input/output interface to the physically distant central computer with knowledge base regarding parameters amenable to patient control in the pain reduction device including: treatment duration, characteristics of the electrical pulse, and patient-selected current intensity. The system can be employed to monitor progress and or control the pain management protocols of one or more patients in a concurrent manner.

The central computer with knowledge-based program and central health provider will receive data and transmit instructions to and from the patient, remote health provider, computer with input/output interface and pain-reduction medical device with input/output interface. Data will be transmitted via the Internet or multiple types of combinations of networks architectures including: local area network, wide area network, and television network (transmitted, broadband or cable, public switched telephone network or integrated services digital network). The information will be formatted with output to a communication device involving various combinations of video and voice. Video conferencing interface involving a camera and microphone located at the knowledge base as well as patient station is also included.

Information regarding the epidemiology of chronic pain, therapeutic interventions and efficacy can also be recorded, stored and analyzed by the knowledge-based program. The effectiveness of different pain treatment protocols for example involving location, frequency of use, duration, and polarity and other treatment parameters will also be statistically analyzed to optimize recommendations.

By having a knowledge base help to generate recommendations as to treatment points, health providers as well as the patient will be able to locate effective acupoints for stimulation. Although location is important, it will not be beyond the abilities of most patients to place TENS electrodes at recommended acupoints because of the spread of current through the local tissues. Settings for the pain reduction device involving parameters including waveform, frequency, duration and polarity are also important. The pain manager program can recommend settings to the provider or at times directly to the patient. In the preferred embodiment, although not necessary or appropriate for all situations, the settings for the pain-reducing device can be directly entered into the pain-reducing medical device via the input/output interface, such as a docking station with the remote computer. If the pain reduction medical device is implanted, there will also be a patient input/output interface in proximity or attached to the patient.

The foregoing and other objects, features and advantages of the invention will become more readily apparent from the following detailed description of a preferred embodiment of the invention that proceeds with reference to the accompanying drawings.

DETAILED DESCRIPTION

Figure 1:
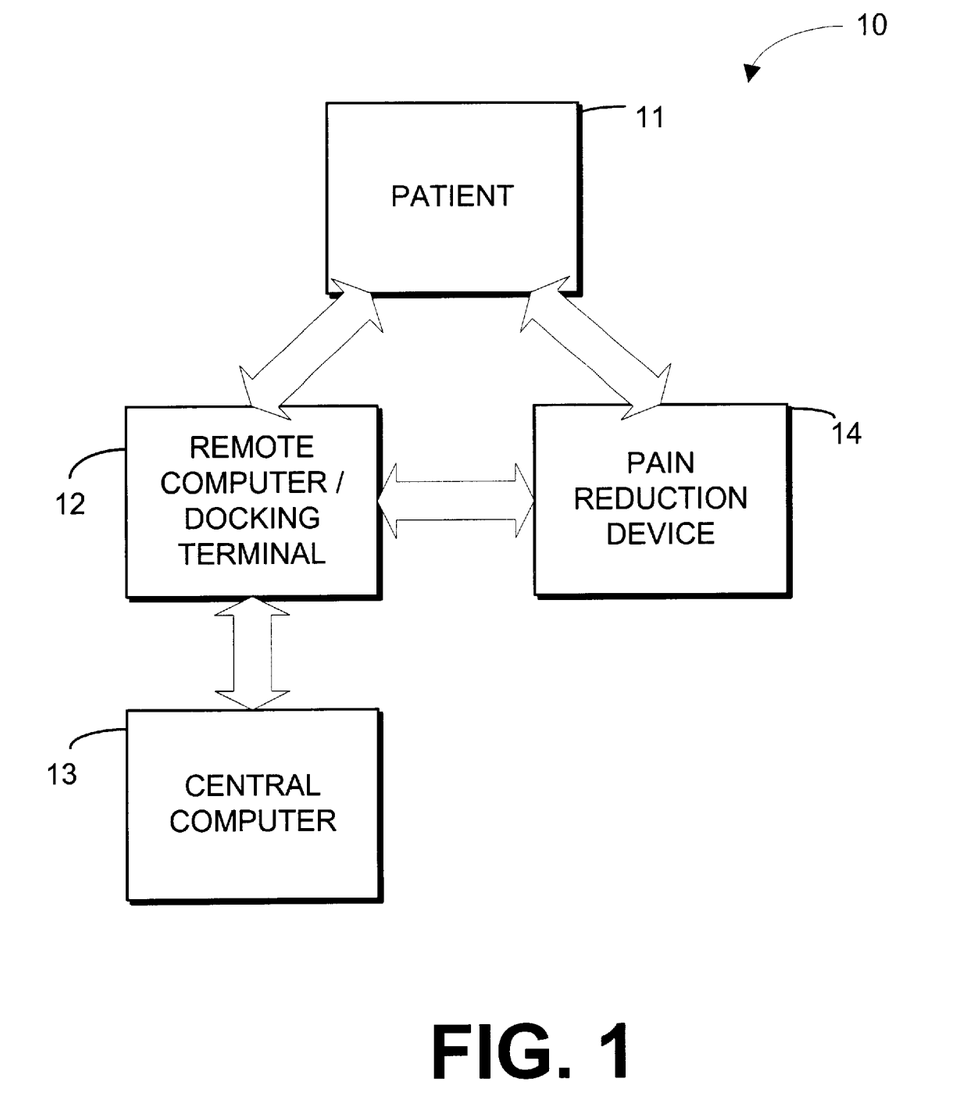
FIG. 1 is a block diagram of the pain management system connections between the patient, remote computer with interface docking terminal, knowledge base and pain-reduction device according to a preferred embodiment of the invention.

A preferred embodiment of the pain management system 10 comprising the relationships involving the use of Internet or combinations of network architectures involving coordination between a patient 11, remote computer with interface docking terminal 12, knowledge base 13 and pain reducing device 14 is shown in FIG. 1. As illustrated, the remote computer with interface docking terminal 12 may be in the patient's home, at the doctor's office or at any medical care facility.

In accordance with the present invention, the patient will enter data of various types through the remote computer with interface docking terminal 12. The data might include information regarding diagnoses, pain location, severity, duration, patient functional status, and psychosocial functioning. Previous treatment experience will also be relevant including: pharmacological pain treatment (pills or other drug-type forms), medical pain treatment, noninvasive or invasive medical treatment (e.g. nerve blocks), physical and massage therapy, pain reduction devices (e.g. TENS), chiropractic manipulation, traditional Chinese Medicine and homeopathy.

The remote computer with interface docking terminal will run analyses at scheduled intervals. Each computer stores the results of those analyses in log files, which may be local to each computer, e.g., in its own disk drives, or at a storage location in the networked system accessible by each computer. The saved pain related information is collected at a location accessible by the master computer. In one embodiment, the location is local to the master computer. Finally, the information from the computer with interface docking terminal 12 is communicated via the Internet to the central master computer containing the knowledge base and pain management program 13.

The knowledge base program 13 will analyze the data and make patient specific-treatment recommendations regarding pain management, in particular: location of optimal acupoints to treat a given chronic pain, treat session utilization parameters (including number of times per day and duration of treatment), and pain reduction device parameters. When the pain-reducing device is a transcutaneous electrical nerve stimulation (TENS) device, settings will be modified including: frequency, duration, polarity and waveform. The preferred waveform parameters include: constant current output despite skin conductance changes, identical positive and negative square waves alternating with each other and having a net output of 0, automatic adjustment of pulse width with increase during low frequency stimulation and increase during high frequency stimulation, automatic adjustment of polarity, fixed and variable time intervals of 3 to 5 seconds of 2 to 4 Hz alternating with fixed and variable time intervals of 3 to 5 seconds of 80 to 100 Hz (with an without symmetrical increase and decrease in wave form). The knowledge base program, in addition to providing information directly to the patient 11 via the remote computer with interface docking terminal 12, will also directly modify settings of the pain reduction device 14.

Figure 2:
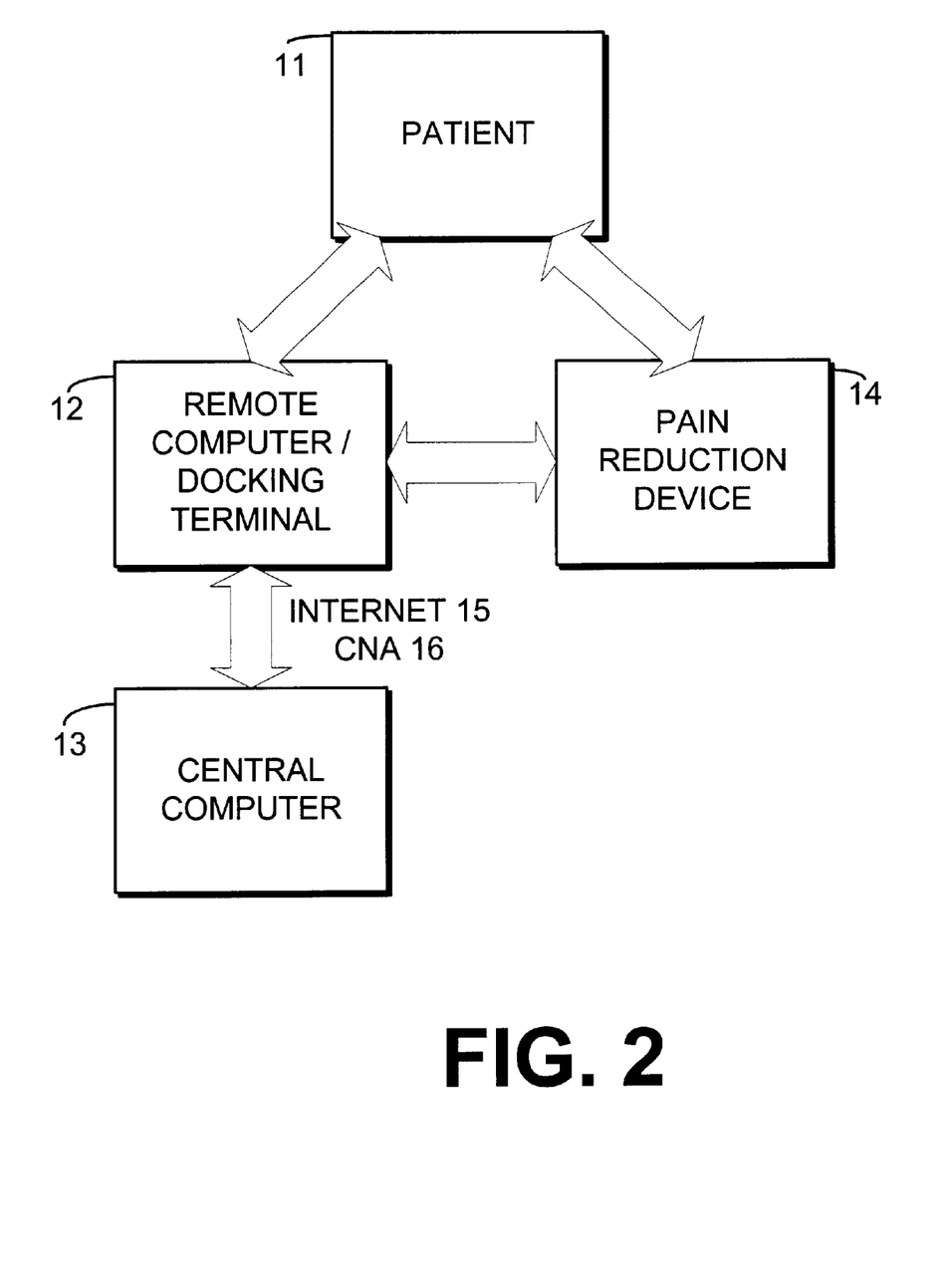
FIG. 2 is a block diagram of connections via the Internet or combinations of network architectures between the patient, remote computer with interface docking terminal, knowledge base, and pain-reducing device.

FIG. 2 is a diagram of the method of using the Internet 15 or combinations of network architectures 16 to connect the interface docking terminal with the knowledge base program. In accordance with the present invention, data of various types is sent to and from the central knowledge base system. It should be noted that the interface docking terminal may be located at any location having access to a communications network. It should also be noted that a plurality of interface docking terminals could communicate with a plurality of central knowledge bases.

The combinations of network architectures includes: local area networks, wide area networks, television networks, transmitted broadband or cable, public switched telephone network and integrated services digital network. It will be apparent that other types of communications protocols are suitable for use with the present invention including dial up modem link, e-mail or RF link.

Figure 3:
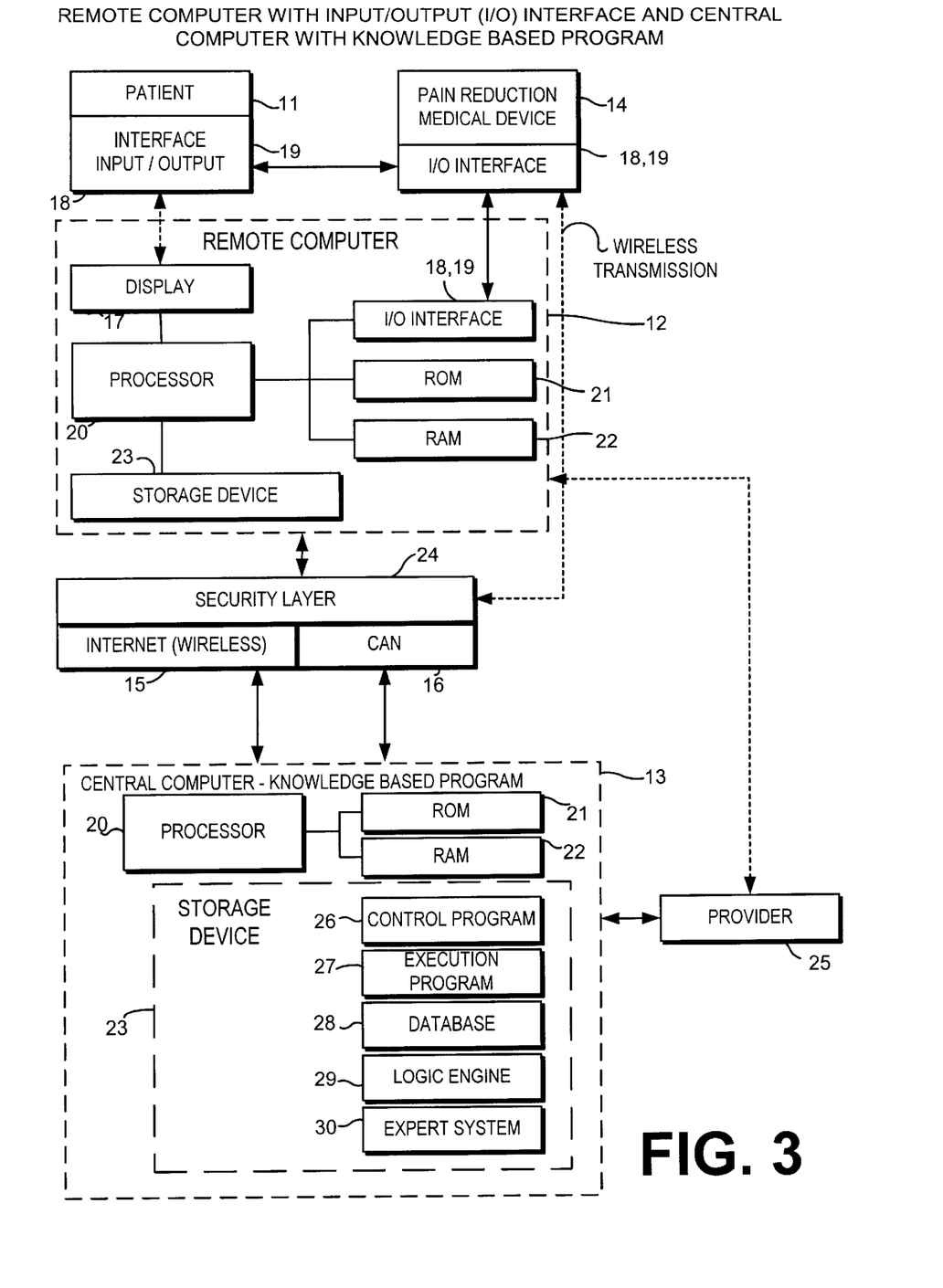
FIG. 3 is a functional schematic block diagram of the components of the central computer with knowledge based program and remote computer with input/output interface.

FIG. 3 is a diagram of the components of the remote computer with input/output interface and central computer with knowledge based program. The remote computer with interface docking station 12 comprises a conventional display 17, which will display a variety of information including clinical information summary and status of the computer system. In one embodiment the display will contain the user input interface 18 and will be jointly embodied as a touch screen CRT. The touch screen CRT displays output 19 to the user and conveys input 18 to the processor by the user contacting the appropriate locations on the screen. In such an embodiment, the user input interface 18 may also comprise other input devices such as keyboard and mouse, video, or voice recognition.

The remote computer 12 input/output (I/O) interface 18,19 is also able to be in direct electrical communication with the pain reduction medical device (PRD) 14 via the input/output interface and controls the flow of data to and from the device. Although the PRD 14 in FIG. 3 is shown directly connected to the remote patient computer 12, it is understood that interface docking terminals such as those well known in the art can be adapted to connected the disclosed PRD to computers to receive programming information.

In another embodiment, the input and output interface 18,19 could communicate with a combination of network architectures 16 including: local area networks, wide area networks, television networks, transmitted broadband or cable, public switched telephone network, integrated services digital network, dial up modem link, e mail or radio frequency (RF) link. If the pain reduction medical device is implanted into the patient, there will be an optional input/output interface 18,19 in proximity or attached to the patient, which will in turn communicate with the input/output interface of the remote computer 12. In one embodiment, the PRD 14 may also communicate via the input/output interface 18,19 directly with the central computer with knowledge based program 13.

The remote computer 12 also comprises a conventional processor 20 with sufficient capacity to perform the functions of the system. The processor 20 is in electrical communication with a read only memory (ROM) 21, which provides initial configuration and verification of the computer system 12 upon start up of the system. The processor 20 is also in further in electrical communication with a random access memory (RAM) 22, which provides short-term storage of data and programming for the processor 20. The processor 20, the ROM 21 and the RAM 22 are defined as the central processing unit of the remote computer 12. The remote computer 12 also comprises a storage device 23, which is a computer usable medium with long-term memory storage capability. In one embodiment, the storage device will be embodied as a combination of floppy disk, compact disk and hard disk (all with appropriate drives). In all of the embodiments, the storage device 23 is in electrical communication with and accessible by the processor 20.

The remote computer 12 will be in electrical connection via a security layer 24 with the central computer with knowledge based program 13. The security layer 24 comprises any standard security scheme or technology. The security layer 24 may be used for all communication system wide. This will, for example, include: patients 11, all pain reduction medical devices 14, remote computer with docking stations 12, central computer with knowledge based program 13 and health care providers 25. In one embodiment the pain reduction medical device 14 with input/output interface will be in direct electrical communication through the security layer via Internet (wireless) 15 or CNA 16 connections.

The central computer with knowledge-based program 13 will have the same components as the remote computer 12: processor 20, ROM 21, RAM 22 and storage device 23. The more sophisticated central computer with knowledge-based program 13 further comprises a control program 26, which is embodied as a computer readable code and directs the processor 20 in performing the functions of the invention. In one presently preferred embodiment, the control program 26 is preferably stored in a computer-usable medium such as the storage device 23. In another alternative embodiment, the control program 26 is stored in an integrated memory circuit, which is in electrical communication with the processor 20.

In yet another embodiment, the control program 26 is partially stored in the ROM 21 and partially stored on the above mentioned storage device 23. In such an embodiment, the processor 20 initially accesses the ROM 21 upon start up of the system. The control program 26 begins verification and configuration of the other storage devices to locate the remainder of the control program 26. The processor 20 is then directed to the appropriate storage device to retrieve the remainder of the control program 26.

The control program 26 encompasses all of the software programming necessary to perform the function of the invention and comprises an execution program 27, database 28, logic engine 29 and expert system 30. Control of the system is transferred primarily between the execution program 27 and the logic engine 29 and expert system 30 in performing the function of the invention.

The execution program 27 commences operation of the system and provides the interface with the user. The execution program 27 prompts the user for all of the inputs including: medical diagnoses, pain characteristic (including severity, characteristics, duration), patient functional status and patient psychosocial profile. Previous experience with evidence and non evidence based treatment modalities including pharmacological pain treatment (pills or other drug-type forms), medical pain treatment, whether the treatment was non invasive or invasive (e.g. nerve blocks), physical and massage therapy, experience with pain reduction devices (e.g. tens), chiropractic manipulation, traditional Chinese Medicine and homeopathy. The user (patient 11 or provider 25) responds to these prompts on the central computer-knowledge based program 13, or remote computer 12 display 17 by entering inputs in the form of parameters defined by the execution program 27. This provides a basis from which the control program 26 may determine the necessary information for the database 28. The execution program 27 assembles the user-entered parameters into data files, which are preferably stored in the RAM 22 for speedy access by the processor 20.

The data files 28 are specific to each patient and recommendations regarding needed acupoints and pain reduction medical device 14 parameters. The execution program 27 may prompt for input and display output in a variety of formats. In one presently preferred embodiment, the execution program includes a graphical user interface (GUI) to elicit responses in a series of prompts. The GUI employs suitable text oriented graphics and icons to elicit responses from a user regarding pain localization, and recommended treatment acupoints.

The logic engine 29 performs the computations in order to allow representations of human and evaluation processes in algorithmic form. The logic engine 29 and the expert system 30 will access the database 28 established by the execution program 27 to retrieve the user-entered information. The database 28, logic engine 29 and expert system 30 may be updated periodically in accordance with currently available expert knowledge. The logic engine 29 will be able to derive solutions for a given set of rules that have been defined for similar cases. After describing the desired performance of a technical system for certain distinct cases by rules, fuzzy logic will apply this knowledge to produce a solution. The logic engine 29 and expert system 30 will respond to patient 11 and professional input 25 regarding level of analysis: manual, semiautomatic or automatic. The expert system 30 will then be used to make specific treatment recommendations including: location of optimal acupoints to treat a given chronic pain, treatment session parameters including number of treatments per day and recommended duration. Pain reduction device settings will also be recommended or directly modified including frequency, duration, polarity and waveform. In the automatic mode, a program will be compiled responsive to analysis of patient data and exported for loading into the PRD 14.

The steps performed by the control program 26 are accomplished through the cooperative interaction of the execution program 27, database 28, logic engine 29 and expert system 30. The processor 20 executes all components of the control program 26.

Figure 4:
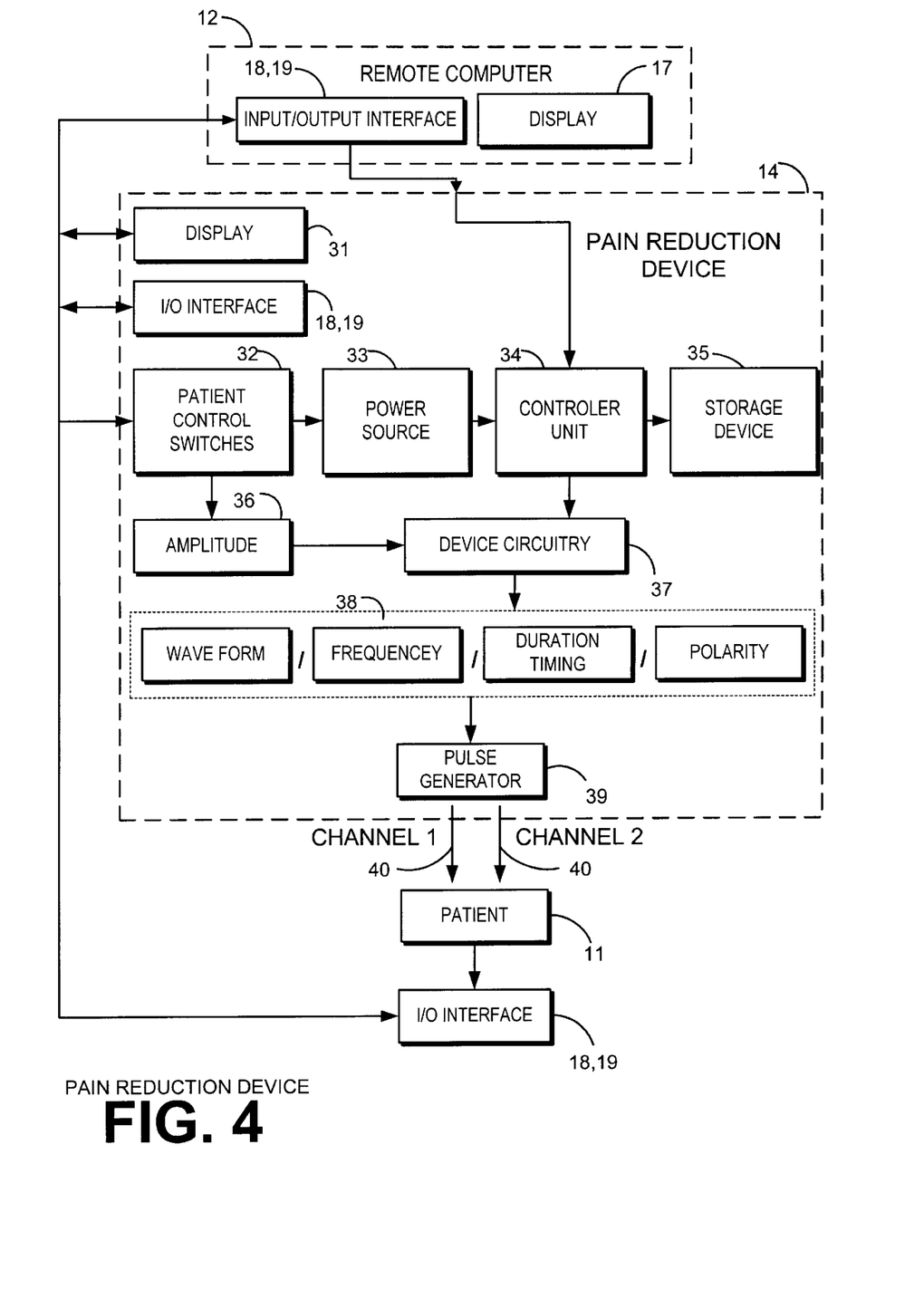
FIG. 4 is a functional schematic block diagram of the components of the pain reduction medical device with input/output interface.

FIG. 4 is a functional schematic diagram of the Pain Reduction Device (PRD) 14. The remote computer 12 also contains as previously described: display 17, input interface 18 and output interface 19. The PRD 14 is a fully functional, self-contained electro-therapy device for treatment of pain. The PRD 14 in the preferred embodiment will be external to the patient, however in an alternative embodiment it may be internal or implanted.

In one embodiment the PRD 14 input/output interface 18,19 will allow the device to be in electrical connection with the I/O interface 18,19 of the remote computer 12. In another embodiment there will be a supplemental I/O interface 18,19 attached to or worn by the patient 11. This will help to ensure optimal electrical connection between the patient 11, PRD 14, the central computer with knowledge based program 13. The need for this additional patient 11 I/O interface 18,19 will probably vary with amplitude 36, characteristics of the waveform 38 used, and location of the electrical stimulus applied to specific acupoints.

The PRD 14 display 31 will be a liquid crystal display (LCD) or other similar display providing a variety of information including: instructions, residual treatment time left to run, characterization of the treatment, level of charge in the batteries and amplitude in analog form of the pulse signal delivered at each of the outputs. The display 31 will also be integrated with patient control switches 32, which in manual mode will operate the self-contained power source 33 and the controller unit 34. When operating in semiautomatic or automatic mode, additional inputs and recommendations will be obtained from the central computer with knowledge-based program 13 and provider 25. The controller unit 34 includes a microprocessor and performs other aspects of the operation of the device using software instructions contained in the storage device 35. Additional memory for the PRD 14 will be obtained from the knowledge based program 13 central computer 25 via the docking station 12, input/output interface 18,19. This will include a variety of previously described electrical connections including Internet (wireless) 15 and CNA 16.

Patient 11 using the display 31 and patient control switches 32 can directly control amplitude 36 of electrical energy delivery system therapeutic impulse on all operational modes (manual, semiautomatic and automatic). Different people require different stimulation levels to produce an acceptable response. Other aspects of the treatment parameters will be controlled by microprocessors contained in device circuitry 37 which will provide an electrical stimulation signal with specified parameters (38) including: wave form, frequency, duration-timing and polarity. Waveform and pulse width compensation will be based on applicable strength-duration curves to vary the range of the peak current delivered as pulses from the device.

Program information obtained from the central computer 13 is transmitted to remote computer 12 and passed through (as through a docking station) to the controller unit 34 of PRD 14 and stored in PRD storage device 35. In use, the program instructions are retrieved from storage device 35 and used to drive device circuitry 37 to produce the recommended TENS signals having characteristics of waveform, frequency, duration and polarity.

In the preferred embodiment there will be constant current output, despite skin conductance changes. There will also be identical positive and negative square waves alternating with each other (with net output being 0). Automatic adjustment of pulse width will increase during low frequency stimulation and decrease during high frequency stimulation. Polarity will be automatically adjusted. The train of pulses forming the stimulation signal will alternate at fixed and variable time intervals of 3 to 5 seconds between high frequency (80–100 Hz) and low frequency (3–5 Hz). This alternation of high and low frequency will occur with and without symmetrical increase and decrease in waveform amplitude. Duration-timing will be preset for approximately 30 minutes, which optimizes typical cycle length for the typical cycle length for endorphin related acupoint stimulation. The patient control switches 32 and display information 31 based on the knowledge based program 13 central computer 25 will provide additional instruction on optimal lead placement and treatment duration. The pulse generator 39 provides patient output 40 via channel 1 and 2.

The electrical signal is applied to the patient transcutaneously by means of wires and surface electrodes, there being one pair per output channel. The preferred electrical output of the present invention is subsequently described and depicted in diagram form in FIGS. 5 and 6. The recommended location of the electrodes to provide pain relief, based on acupoints, will be indicted on the display 17 as recommended by the central computer with knowledge based program 13 after review and in conjunction with the provider 25.

Although the present invention has been described with reference to preferred embodiments, changes may be made in form without departing from the scope of the invention.

Figure 5:
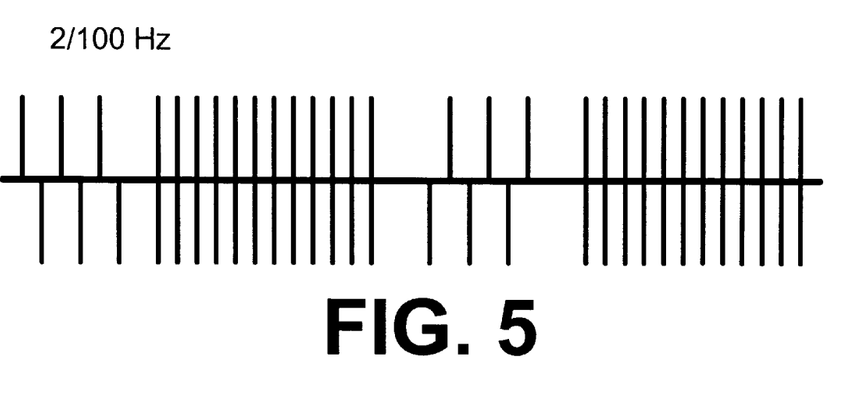
FIG. 5 is a representation of alternating 3 seconds of 2 Hz and 3 seconds of 100 Hz waveforms transmitted through the transcutaneous electrical never stimulation (TENS) device.

FIG. 5 is a representation of alternating 3 seconds of 2 Hz and 3 seconds of 100 Hz waveforms.

Figure 6:
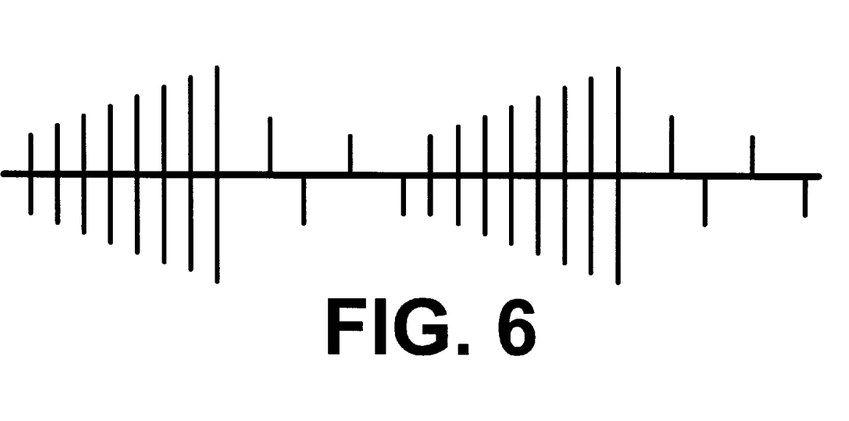
FIG. 6 is a representation of waveforms of alternating 3 seconds of 2 Hz and 3 seconds of 100 Hz with amplitude modulation consisting of symmetrical increase and decrease in waveform for 3 seconds within the TENS device.

FIG. 6 is a representation of waveforms of alternating 3 seconds of 2 Hz and 3 seconds of 100 Hz with amplitude modulating consisting of symmetrical increase and decrease in waveform for 3 seconds.

CLINICAL EXAMPLES

Example 1

A 58-year-old male was thought by his physician to have developed post laminectomy syndrome with 8/10 pain (1 mild to 10 severe) radiating into the right lumbar 5 nerve root distribution with pain over the sacro-iliac joint, hip, lateral thigh and leg. After a trial of physical therapy, nerve blocks and various pharmaceuticals including non-steroidal anti-inflammatory drugs, muscle relaxants, membrane stabilizers and narcotics, the patient continued to have 8–9/10 pain. The remote physician provider recommended the transcutaneous electrical nerve stimulation (TENS) programmable pain reduction medical device (PRD).

The patient and remote physician input entered clinical data in the remote computer display, which via the input-output (I/O) interface was transmitted by combinations of network architectures (CNA) to the central computer with knowledge based program. By using fuzzy logic and the database of the present invention, the program also interacted and inquired about a number of additional clinical parameters including: dysthesia, function, autonomic dysfunction, temperature, discoloration and edema. The expert system, with central provider review, made the correct diagnosis of reflex sympathetic dystrophy. The knowledge based program then provided a recommended set of stimulation parameters consisting of 2 Hz alternating with 100 Hz frequency, with ascending and descending modulation, which were directly transmitted through the input/output interface to the TENS PRD. Recommendations for specific acupoints and treatment plan for reflex sympathetic dystrophy were also transmitted to the patient and remote physician by the remote computer display. The patient had a dramatic reduction in pain, which varied from 2–4/10, depending on activity. Subsequent subtle changes in location of pain and associated symptoms, along with documented response to therapy, resulted in regular updated changes in recommended stimulation parameters an acupoints. The patient continues wear the TENS PRD on his belt for daily treatment while at work and home.

Example 2

A 45-year-old female from Canada has lived with 6–8/10 pain at multiple locations for over 10 years. She had given up on finding relief from medical doctor providers, and had not found pain relief from a variety of alternative therapies including: naturopathy, homeopathy, vitamins, health foods, chiropractic and traditional Chinese Medicine. Acupuncture did seem to help to control pain and maintain a reasonable functional status, but required twice-weekly visits to the acupuncturist and was expensive.

The patient logged on to a web site coupled to the central computer and entered her symptoms and pain characteristics. The program used the fuzzy logic engine to interpret clinical data and the database and expert system in real time to prompt and request additional clinical information. Based on the symptoms and location of pain, the central computer, with central provider review, diagnosed fibromyalgia. The patient was provided with educational material regarding fibromyalgia and ordered a TENS PRD. The database and expert system makes therapeutic recommendations, reviewed by the central provider, regarding treatment and optimal acupoint location and also direct sets the treatment parameters for the TENS PRD via the input/output interface. The patient was treated with 4 Hz alternating with 80 Hz frequency of constant amplitude at various specific acupoints. Because of the involved fibromyalgia trigger points, the complexity of rotating treatment locations and stimulation parameters, optimal treatment would only be possible was possible only because of the data base and decision rules contained in the expert system.

The (fuzzy) logic engine continued to be needed to analyze new and continuously changing clinical data entered by patient during the course of treatment and extracted from the pain reduction medical device. The expert system was then able to optimize recommended treatment plan, location of acupoints and directly set output parameters for the PRD. By optimizing treatment, the patient and experienced a 50% reduction in pain levels and 80% improvement in functional status.

Example 3

A 60-year-old male with inoperable pancreatic cancer had constant 9/10 pain. Pain control required long and short acting narcotics, but nausea prevented adequate dosage. The remote provider recommended that the patient have an implanted pump PRD 14 to deliver narcotics, and to use a TENS PRD to help with nausea and pain.

The patient and provider entered the clinical information at the remote computer I/O interface with wireless Internet connection. The central computer with knowledge-based program used the fuzzy logic engine to analyze the clinical data added to the database. The expert system used the clinical and therapeutic database to formulate therapeutic recommendations, which were reviewed by a central provider. Recommendations and treatment plan were transmitted via the Internet to the remote computer for the patient and remote physician provider. Settings for the implanted pump PRD, after review by central provider, were transmitted to the I/O interface worn by the patient the I/O interface of the implanted pump PRD. The expert system recommended variable combinations of morphine sulfate and Versed to optimize pain control. The expert system also recommended acupoints to the patient and provider via combinations of network architecture.

TENS PRD parameters were directly set via wireless internet with 2 Hz alternating every 3 seconds with 100 Hz with ascending and descending amplitude modulation to help with both nausea and pain control. By using the patient I/O interface, the recommended therapeutic changes based on variable pain and activity levels allowed the patient to achieve substantially improved pain control and functional status during progression to hospice and his demise.

Having described and illustrated the principles of the invention in a preferred embodiment thereof, it should be apparent that the invention can be modified in arrangement and detail without departing from such principles. The invention should not be limited, for instance, to TENS devices but rather can be applied to any medical device having parameters than can be remotely programmed responsive to locally or remotely input patient criteria. One example is a drug-dispensing module in which the syringe is electronically filled to a certain amount prior to injection responsive to patient data. Another is a drip valve responsive to patient data. Accordingly, I claim all modifications and variation coming within the spirit and scope of the following claims.

What is claimed is:

1. A method for programming a pain reduction device over a network, the network comprising:
   a client computer including a user interface for entering patient information;
   a remote computer including data analysis means for matching an appropriate treatment regiment with the entered patient information; and
   transmission means for transmitting said patient information from said user interface over a network to said remote computer and transmitting said appropriate treatment regiment, responsive to the received patient information, to said user interface, and the pain reduction device comprising:
      memory means for storing program information;
      a treatment interface for administering medical treatment to a patient;
      microprocessor means for administering treatment through the treatment interface according to the program information stored in the memory means, said method comprising the steps of:
         coupling the pain reduction device to the client computer;
         entering patient information into the user interface;
         transmitting the patient information to the remote computer;
         determining an appropriate treatment regiment responsive to the patient information and transmitting the appropriate treatment regiment to the client computer, said treatment regiment including program information for operating the pain reduction device;
         storing the program information within the memory means of the pain reduction device; and
         operating the pain reduction device under control of the program information on a patient through the treatment interface, wherein the treatment interface includes electrodes and the step of operating the pain reduction device includes:
            applying the electrodes to the patient for transmission of electrical stimulus through the skin of the patient;
            generating signals within the pain reduction device characterized by a high frequency signal alternating with a concurrent low frequency stimulus signal; and
            transmitting the signals through the electrodes for treating chronic pain.

2. The method of claim 1 wherein the high frequency signal is between 80–100 Hz and the low frequency signal is between 2–5 Hz.

3. The method of claim 1 wherein the generating step includes maintaining each of the high frequency and low frequency signals is for a period of between 3–5 seconds.

4. The method of claim 1 further including the step of symmetrically increasing and decreasing a waveform amplitude of the high frequency and low frequency signal.

5. The method of claim 1 further including the step of increasing a pulse width of the low frequency signal during low frequency stimulation and decreasing the pulse width of the high frequency signal during high frequency stimulation.

6. The method of claim 1 wherein the step of transmitting the patient information to the remote computer occurs over transmission means taken from the group comprising local area networks, wide area networks, television networks (transmitted, broadband or cable), public switched telephone networks, and integrated services digital network.

7. A method for programming a medical device over a network, the network comprising:
   a client computer including a graphic user interface and display for entering patient information;
   a remote computer including data analysis means for matching an appropriate treatment regiment with the entered patient information; and
   transmission means for transmitting said patient information from said user interface over a network to said remote computer and transmitting said appropriate treatment regiment, responsive to the received patient information, to said user interface, and the medical device comprising:
      memory means for storing program information;
      a treatment interface including electrodes for administering medical treatment to a patient;
      microprocessor means for administering treatment through the treatment interface according to the program information stored in the memory means, said method comprising the steps of:
         coupling the medical device to the client computer;
         entering patient information into the graphic user interface;
         transmitting the patient information to the remote computer;
         determining an appropriate treatment regiment responsive to the patient information and transmitting the appropriate treatment regiment to the client computer, said treatment regiment including program information for operating the medical device;
         storing the program information within the memory means of the medical device; and
         operating the medical device under control of the program information on a patient through the treatment interface, including applying the electrodes to the patient for transmission of electrical stimulus through the skin of the patient;
         generating signals within the medical device characterized by a high frequency signal alternating with a concurrent low frequency stimulus signal; and transmitting the signals through the electrodes for treating chronic pain.

8. The method of claim 7 wherein the high frequency signal is between 80–100 Hz and the low frequency signal is between 2–5 Hz.

9. The method of claim 7 wherein the generating step includes maintaining each of the high frequency and low frequency signals is for a period of between 3–5 seconds.

10. The method of claim 7 further including the step of symmetrically increasing and decreasing a waveform amplitude of the high frequency and low frequency signal.

11. The method of claim 7 further including the step of increasing a pulse width of the low frequency signal during low frequency stimulation and decreasing the pulse width of the high frequency signal during high frequency stimulation.

12. The method of claim 7 wherein the step of storing the program information includes directly storing the program information from the transmitting step without human intervention.

13. A method for programming a medical device over a network, the network comprising:
   a client computer including a user interface for entering patient information;
   a remote computer including data analysis means for matching an appropriate treatment regiment with the entered patient information; and transmission means for transmitting said patient information from said user interface over a network to said remote computer and transmitting said appropriate treatment regiment, responsive to the received patient information, to said user interface, and the medical device comprising:

memory means for storing program information;

a treatment interface including electrodes for administering medical treatment to a patient;

microprocessor means for administering treatment through the treatment interface according to the program information stored in the memory means, said method comprising the steps of:

coupling the medical device to the client computer;

entering patient information into the user interface;

transmitting the patient information to the remote computer;

determining an appropriate treatment regiment responsive to the patient information and transmitting the appropriate treatment regiment to the client computer, said treatment regiment including program information for operating the medical device;

directly storing the program information within the memory means of the medical device from the transmitting step; and operating the medical device under control of the program information on a patient through the treatment interface, including applying the electrodes to the patient for transmission of electrical stimulus through the skin of the patient;

generating signals within the medical device characterized by a high frequency signal alternating with a concurrent low frequency stimulus signal; and transmitting the signals through the electrodes for treating chronic pain.

14. The method of claim 13 wherein the high frequency signal is between 80–100 Hz and the low frequency signal is between 2–5 Hz.

15. The method of claim 13 wherein the generating step includes maintaining each of the high frequency and low frequency signals is for a period of between 3–5 seconds.

16. The method of claim 13 further including the step of symmetrically increasing and decreasing a waveform amplitude of the high frequency and low frequency signal.

17. The method of claim 13 further including the step of increasing a pulse width of the low frequency signal during low frequency stimulation and decreasing the pulse width of the high frequency signal during high frequency stimulation.

* * * * *

UNITED STATES PATENT AND TRADEMARK OFFICE
CERTIFICATE OF CORRECTION

PATENT NO. : 6,662,051 B1
DATED : December 9, 2003
INVENTOR(S) : Eraker et al.

It is certified that error appears in the above-identified patent and that said Letters Patent is hereby corrected as shown below:

Title page,
Item [56], References Cited, U.S. PATENT DOCUMENTS, "2,622,601 A 2/1952 Nemee ..... 128/422" should read -- 2,622,601 A 12/1952 Nemee .....128/422 --; and "4,712,562 A 12/1987 Ohayou ..... 128/670" should read -- 4,712,562 A 12/1987 Ohayon ..... 128/670 --.

Column 6,
Line 53, "with. input/output" should read -- with input/output --.

Column 14,
Line 43, "Versed to" should read -- V ersed to --.

Signed and Sealed this

Twentieth Day of July, 2004

JON W. DUDAS
*Acting Director of the United States Patent and Trademark Office*